(12) United States Patent
Chen et al.

(10) Patent No.: US 11,826,136 B2
(45) Date of Patent: Nov. 28, 2023

(54) METHOD FOR DETERMINING ISCHEMIC STATUS OR ASSESSING STROKE ONSET TIME OF A BRAIN REGION

(71) Applicant: TAIPEI MEDICAL UNIVERSITY, Taipei (TW)

(72) Inventors: Cheng-Yu Chen, Taipei (TW); Hsiao-Wen Chung, Taipei (TW); Duen-Pang Kuo, Taipei (TW); Chia-Feng Lu, New Taipei (TW); Yu-Chieh Jill Kao, Taipei (TW)

(73) Assignee: TAIPEI MEDICAL UNIVERSITY, Taipei (TW)

( * ) Notice: Subject to any disclaimer, the term of this patent is extended or adjusted under 35 U.S.C. 154(b) by 0 days.

(21) Appl. No.: 17/548,460

(22) Filed: Dec. 10, 2021

(65) Prior Publication Data

US 2022/0095945 A1    Mar. 31, 2022

Related U.S. Application Data

(62) Division of application No. 15/662,807, filed on Jul. 28, 2017, now Pat. No. 11,229,375.

(51) Int. Cl.
| | |
|---|---|
| *A61B 5/00* | (2006.01) |
| *A61B 5/055* | (2006.01) |
| *G01R 33/48* | (2006.01) |
| *G06T 7/00* | (2017.01) |
| *G01R 33/563* | (2006.01) |

(52) U.S. Cl.
CPC ............ *A61B 5/055* (2013.01); *A61B 5/0042* (2013.01); *A61B 5/7246* (2013.01); *A61B 5/7264* (2013.01); *G01R 33/4806* (2013.01); *G06T 7/0012* (2013.01); *G01R 33/56341* (2013.01); *G06T 2207/10088* (2013.01); *G06T 2207/30016* (2013.01)

(58) Field of Classification Search
CPC ..... A61B 5/055; A61B 5/0042; A61B 5/7264; A61B 5/7246
See application file for complete search history.

(56) References Cited

PUBLICATIONS

Kuo et al (Differentiation of the Infarct Core from Ischemic Penumbra within the First 4.5 Hours, Using Diffusion Tensor Imaging-Derived Metrics: A Rat Model); Korean Journal of Radialogy. 2017 (Year: 2017).*

* cited by examiner

*Primary Examiner* — Joel F Brutus
(74) *Attorney, Agent, or Firm* — WPAT, P.C.

(57) ABSTRACT

The invention relates to a method for determining ischemic status. The method comprises acquiring magnetic resonance diffusion tensor matrices and obtaining a relative decrease of diffusion magnitude due to the ischemic status from the magnetic resonance diffusion tensor matrices. The invention also relates to a method for assessing stroke onset time. The method comprises acquiring magnetic resonance diffusion tensor matrices and obtaining a relative decrease of pure anisotropy due to stroke from the magnetic resonance diffusion tensor matrices.

8 Claims, 8 Drawing Sheets

METHOD FOR DETERMINING ISCHEMIC STATUS OR ASSESSING STROKE ONSET TIME OF A BRAIN REGION

BACKGROUND OF THE INVENTION

1. Field of the Invention

The invention relates to uses of magnetic resonance imaging (MRI). Particularly, the invention relates to a method for determining ischemic status or assessing stroke onset time of a brain region by magnetic resonance diffusion tensor matrices.

2. Description of the Related Art

Clinically, the golden hour of acute ischemic stroke is from the first minutes after onset to the next 3-4.5 hours. Hence, identification and differentiation of infarct core (the necrosis region due to ischemia) and reversible ischemic penumbra by non-invasive examination within a shortest time is critical for assessing the necessity of surgical intervention.

On the other hand, in a significant proportion of patients, the exact time of stroke onset is unknown. Up to about one-quarter of the acute ischemic stroke patients, they either wake up with stroke symptoms or are found without conscious, and the stroke onset time cannot be ascertained. A clinical tool for estimating stroke onset time is thus required to determine whether the patients are still within the golden hour eligible for thrombolytic therapy.

Currently, identification and differentiation of infarct core and ischemic penumbra is achieved through magnetic resonance perfusion diffusion mismatch (PDM), which requires two pulse sequences for magnetic resonance imaging: perfusion weighted imaging and diffusion weighted imaging. Since an MRI contrast agent is needed in performing magnetic resonance perfusion diffusion mismatch scanning, a blood biochemical test of kidney function of the patient is required before injection of the MRI contrast agent. The patient must wait for the blood biochemical result, and the golden hour easily passes. Furthermore, the patient also needs to bear the cost and risk of MM contrast agent, and the medical labor rises thereby. After imaging, the two images should be overlapped and the resolution should be adjusted with a professional and processing platform. However, such image processing may result in additional errors. Therefore, the conventional clinical tool for identification and differentiation of infarct core and ischemic penumbra is time-consuming and costly.

In addition, there is not yet a clinical tool for assessing the stroke onset time, and an objective index for the golden hour of acute ischemic stroke is still absent. Thus the clinical judgement of surgical intervention is difficult.

SUMMARY OF THE INVENTION

The present invention relates to a method for determining the position and size of infarct core and ischemic penumbra of acute ischemic stroke or for estimating the stroke onset time by a single pulse sequence of diffusion tensor imaging (DTI) of magnetic resonance imaging.

The present invention relates to a method for determining ischemic status of a brain region, comprising:
 acquiring magnetic resonance diffusion tensor matrices of the brain region and of a normal brain tissue, wherein the normal brain tissue and the brain region belong to the same brain tissue type;
 obtaining diffusion magnitude (L) of the brain region ($L_i$) and diffusion magnitude of the normal brain tissue ($L_n$) from the magnetic resonance diffusion tensor matrices; and
 calculating a relative decrease of $L_i$ to $L_n$, and the ischemic status is determined by the relative decrease of $L_i$ to $L_n$.

The present invention relates to a method for establishing an index of given ischemic status, comprising:
 determining ischemic status of a brain region having the given ischemic status according to the method for determining ischemic status of a brain region for obtaining the relative decrease of $L_i$ to $L_n$; which relative decrease of $L_i$ to $L_n$ is the index of the given ischemic status.

The present invention relates to an index of given ischemic status, which is established by the method for establishing the index of given ischemic status.

The present invention relates to an index group comprising a plurality of the indices of given ischemic status as mentioned above.

The present invention relates to a method for identifying ischemic status of a test brain region, comprising:
 determining ischemic status of the test brain region according to the method for determining ischemic status of a brain region for obtaining a relative decrease of $L_{it}$ to $L_{nt}$;
 comparing the relative decrease of $L_{it}$ to $L_{nt}$ with the index of given ischemic status or index group as mentioned above to identify the ischemic status of the test brain region.

The present invention relates to a method for profiling ischemic status of a brain in a subject, the brain comprising a plurality of test brain regions, which method comprises:
 acquiring a brain map of the brain;
 identifying ischemic status of the plurality of test brain regions as mentioned above, and correlating the ischemic status of the plurality of test brain regions to obtain an ischemic status map; and correlating the brain map and ischemic status map to profile the ischemic status of the brain.

The present invention relates to a method for establishing a discriminating index of two different given ischemic status, comprising:
 determining ischemic status of a first brain region having a first given ischemic status according to the method for determining ischemic status of a brain region for obtaining the relative decrease of the diffusion magnitude of the first brain region ($L_{i1}$) to the diffusion magnitude of the normal brain tissue ($L_{n1}$);
 determining ischemic status of a second brain region having a second given ischemic status according to the method for determining ischemic status of a brain region for obtaining the relative decrease of the diffusion magnitude of the second brain region ($L_{i2}$) to the diffusion magnitude of the normal brain tissue ($L_{n2}$); and
 analyzing the relative decrease of $L_{i1}$ to $L_{n1}$ and the relative decrease of $L_{i2}$ to $L_{n2}$ in statics to obtain a threshold value of the relative decrease of diffusion magnitude for discriminating against each other as the discriminating index of two different given ischemic status.

The present invention relates to a discriminating index of two different given ischemic status, which is established by the method for establishing a discriminating index of two different given ischemic status.

The present invention relates to a method for identifying ischemic status of a test brain region, comprising:

determining ischemic status of the test brain region according to the method for determining ischemic status of a brain region for obtaining a relative decrease of $L_{it}$ to $L_{nt}$;

comparing the relative decrease of $L_{it}$ to $L_{nt}$ with the discriminating index of two different given ischemic status as mentioned above to identify the ischemic status of the test brain region.

The present invention relates to a method for assessing stroke onset time of a brain region, comprising:

acquiring magnetic resonance diffusion tensor matrices of the brain region and of a normal brain tissue, wherein the normal brain tissue and the brain region belong to the same brain tissue type;

obtaining pure anisotropy (q) of the brain region ($q_i$) and pure anisotropy of the normal brain tissue ($q_n$) from the magnetic resonance diffusion tensor matrices; and calculating a relative decrease of $q_i$ to $q_n$, and the assessing stroke onset time is determined by the relative decrease of $q_i$ to $q_n$;

wherein ischemic status of stroke is infarct core.

The present invention relates to a method for establishing an index of assessing stroke onset time, comprising:

providing a plurality of brain regions having a plurality of given stroke onset time; wherein the plurality of brain regions belong to the same brain tissue type;

assessing stroke onset time of the plurality of brain regions having the plurality of given stroke onset time according to the method for assessing stroke onset time of a brain region for obtaining the plurality of relative decrease of $q_i$ to $q_n$;

obtaining a curve of the relative decrease of $q_i$ to $q_n$ versus stroke onset time as the index of assessing stroke onset time.

The present invention relates to an index of assessing stroke onset time, which is established by the method for establishing an index of assessing stroke onset time.

The present invention relates to an index group comprising a plurality of the indices of assessing stroke onset time as mentioned above.

The present invention relates to a method for assessing stroke unset time of a test brain region, comprising:

assessing stroke unset time of the test brain region according to the method for assessing stroke onset time of a brain region for obtaining the relative decrease of $q_{it}$ to $q_{nt}$;

analyzing the relative decrease of $q_{it}$ to $q_{nt}$ with the index of assessing stroke onset time or index group as mentioned above to assessing the stroke unset time of the test brain region.

BRIEF DESCRIPTION OF THE DRAWINGS

FIGS. 1A to 1D show serial L (FIG. 1A), q (FIG. 1B), FA (FIG. 1C), and T2WI (FIG. 1D) maps of a rat for demonstrating the spatiotemporal evolutions. As shown in the figures, the L and q maps showed significant hypointensities on the ischemic lesion, while FA maps displayed an initial elevation (red arrows) of the ischemia with a later reduction (white arrows) by 6.5 hours. T2WI showed progressively minor increase of intensity in the ischemia areas over time.

DETAILED DESCRIPTION OF THE INVENTION

A single diffusion tensor imaging pulse sequence of magnetic resonance imaging is used in the invention for identifying and differentiating brain regions of different ischemic status (e.g. infarct core, ischemic penumbra and normal tissue) more easily and more conveniently. The conventional pulse sequences of perfusion weighted imaging and diffusion weighted imaging are replaced by the single pulse sequence, and the complicated image overlapping and adjusting is avoided, while the errors are eliminated also. Furthermore, since the magnetic resonance perfusion diffusion mismatch scanning is avoided, the MRI contrast agent is omitted in the invention. Specifically, a blood biochemical test of kidney function and injection of MRI contrast agent can also be avoided, thus significantly reducing time, cost, risk and labor.

The present invention relates to a method for determining ischemic status of a brain region, comprising:

acquiring magnetic resonance diffusion tensor matrices of the brain region and of a normal brain tissue, wherein the normal brain tissue and the brain region belong to the same brain tissue type;

obtaining diffusion magnitude (L) of the brain region ($L_i$) and diffusion magnitude of the normal brain tissue ($L_n$) from the magnetic resonance diffusion tensor matrices; and calculating a relative decrease of $L_i$ to $L_n$, and the ischemic status is determined by the relative decrease of $L_i$ to $L_n$.

As used herein, the term "ischemic status" refers to level or degree of restriction in blood supply to brain tissues. For example, the ischemic status can be defined according to a value of cerebral blood flow reduction (rCBF), which is a cerebral blood flow rate of a sample region relative to that of a normal region. In an embodiment of the present invention, ischemic penumbra is defined as regions showing rCBF values <54%, and infarct core is identified as regions showing rCBF values <54%. As can be appreciated by a person of ordinary skill in the art, the threshold for discriminating normal tissue, ischemic penumbra and infarct core can be adjusted according to needs.

The brain region according to the invention may be located within the cerebrum, brainstem, and cerebellum; preferably the cerebrum. According to cell types, cell distribution, function, or cell density, the brain may be further divided into several brain areas having brain tissue types. In one embodiment of the invention, the brain tissue type is a superficial cortex, a subcortical tissue or a white matter.

Magnetic resonance imaging according to the invention is a medical imaging technique used in radiology to form pictures of the anatomy and the physiological processes of the body in both health and disease. Magnetic resonance imaging is performed with a MRI scanner which uses strong magnetic fields, radio waves, and field gradients to generate images of the inside of the body. Generally, the images are generated with a computer for calculating data of each voxel.

Diffusion magnetic resonance imaging is an imaging method that uses diffusion of water molecules to generate contrast in MR images. According to the invention, diffusion MRI is used for assessing the ischemic status.

Diffusion tensor matrix is used to represent the condition of the diffusion of water molecules of an area (such as a voxel) in MRI. Commonly, the diffusion tensor matrix is obtained by applying diffusion gradients along at least 6-non-collinear orientations and a diffusion gradient without diffusion weighting.

In one embodiment of the present invention, diffusion tensor images generated by diffusion magnetic resonance imaging include at least 6 volumes with diffusion gradients applied along 6-non-collinear orientations and at least one volume without diffusion weighting. Then, diffusion tensor matrices are obtained from these images.

Several geometrical diffusion measures such as linear anisotropy, planar anisotropy, and spherical anisotropy or isotropy can be applied according to the invention. Preferably, the diffusion tensor images are generated with a pulse sequence of echo planar imaging. Therefore, the magnetic resonance diffusion tensor matrices are obtained by magnetic resonance imaging scanning the brain region using echo-planar imaging. Therefore, the magnetic resonance diffusion tensor matrices are obtained by magnetic resonance imaging scanning the brain region using a multi-shot technique.

The diffusion magnitude L is defined as $L=\sqrt{\lambda_1^2+\lambda_2^2+\lambda_3^2}$, wherein $\lambda_1$, $\lambda_2$, and $\lambda_3$ are the eigenvalues of the diffusion tensor matrices, and $\bar{\lambda}$ is the mean diffusion.

In a preferred embodiment of the invention, the method for determining ischemic status of the brain region according to the invention further comprises acquiring a brain tissue type map. Preferably, the brain tissue type map is obtained from the diffusion tensor imaging. In one preferred embodiment of the invention, the brain tissue type map is obtained by fractional anisotropy (FA) mapping calculated from the magnetic resonance diffusion tensor matrices. The fractional anisotropy FA is defined as $$FA = \sqrt{\frac{3}{2}} \frac{q}{L},$$

wherein q represents pure anisotropy. The pure anisotropy is defined as $q=\sqrt{(\lambda_1-\bar{\lambda})^2+(\lambda_2-\bar{\lambda})^2+(\lambda_3-\bar{\lambda})^2}$. In the above equations, $\lambda$ are the eigenvalues of the diffusion tensor matrices, and $\bar{\lambda}$ is the mean diffusion. The fractional anisotropy mapping is obtained by calculating FA value voxel by voxel using the diffusion tensor matrices.

In one embodiment of the invention, an atlas-based tissue classification method is performed to identify the brain tissue types within each image voxel. In the atlas-based tissue classification method, an FA template is co-registered and resampled to a test subject's FA map using a 12-parameter affine transformation. The estimated transformation matrix is then applied to the corresponding tissue atlas to acquire subject-specific tissue map. The regions of superficial cortex, white matter, and subcortical tissue are extracted from the subject-specific tissue map.

As used herein, the term "a normal brain tissue" refers to a brain area where blood supply is normal without restriction. For example, the normal brain tissue can be defined according to a normal value of cerebral blood flow without ischemia. In other word, the normal brain tissue is a tissue without afflicting with ischemic stroke. The normal brain tissue according to the invention is applied as a control group or background for determining the ischemic status of the brain region. As a reason, the normal brain tissue and the brain region belong to the same brain tissue type.

Due to the complexity of brain, it is preferably that the difference between the normal brain tissue and the brain region afflicting with ischemic stroke is only ischemic status. In one embodiment of the invention, the brain region and the normal brain tissue belong to the same brain tissue type in an atlas-based tissue classification method. Preferably, the normal brain tissue is a contralateral homologous tissue of the brain region.

According to the invention, the diffusion magnitude of the brain region ($L_i$) and diffusion magnitude of the normal brain tissue ($L_n$) are both obtained from the magnetic resonance diffusion tensor matrices and a relative decrease of $L_i$ to $L_n$ is further calculated for determining the ischemic status.

Preferably, the relative decrease of $L_i$ to $L_n$ is $(L_i-L_n)/L_n \times 100\%$.

The present invention also relates to a method for establishing an index of given ischemic status, comprising:
determining ischemic status of a brain region having the given ischemic status according to the method for determining ischemic status of a brain region for obtaining the relative decrease of $L_i$ to $L_n$; which relative decrease of $L_i$ to $L_n$ is the index of the given ischemic status.

As used herein, the term "an index" refers to a marker representing a specific condition. The index according to the invention is helpful to provide an objective clinic value.

As used herein, the term "given ischemic status" refers to an ischemic condition which is identified or defined. For example, a cerebral blood flow rate of the given ischemic status relative to that of a normal condition is identified or defined. Preferably, the given ischemic status is defined according to cerebral blood flow. More preferably, the given ischemic status is defined by magnetic resonance imaging scanning the brain region using dynamic susceptibly contrast (DSC) perfusion imaging.

In one preferred embodiment of the invention, the method for establishing the index of given ischemic status comprises:

determining ischemic status of a plurality of brain regions having the given ischemic status according to the method for determining ischemic status of a brain region for obtaining an average of the plurality of relative decrease of $L_i$ to $L_n$.

The plurality of brain regions may be obtained from one subject or from different subject. In order to establish a proper index of the given ischemic status, the source, location or number of the plurality of brain regions is preferably representative.

Due to the complexity of brain, the plurality of brain regions preferably belong to the same brain tissue type.

Preferably, for each brain tissue type, a specific index of given ischemic status is established. For example, an index of infarct core in the superficial cortex, white matter, or subcortical tissue is established separately; an index of ischemic penumbra in the superficial cortex, white matter, or subcortical tissue is established separately.

The present invention relates to an index of given ischemic status, which is established by the method for establishing the index of given ischemic status as mentioned above.

The present invention also relates to an index group comprising a plurality of the indices of given ischemic status as mentioned above. Preferably, each of the given ischemic status is different.

The present invention relates to a method for identifying ischemic status of a test brain region, comprising:
  determining ischemic status of the test brain region according to the method for determining ischemic status of a brain region for obtaining a relative decrease of $L_{it}$ to $L_{nt}$;
  comparing the relative decrease of $L_{it}$ to $L_{nt}$ with the index of given ischemic status or index group as mentioned above to identify the ischemic status of the test brain region.

The present invention relates to a method for profiling ischemic status of a brain in a subject, the brain comprising a plurality of test brain regions, which method comprises:
  acquiring a brain map of the brain;
  identifying ischemic status of the plurality of test brain regions as mentioned above, and correlating the ischemic status of the plurality of test brain regions to obtain an ischemic status map; and
  correlating the brain map and ischemic status map to profile the ischemic status of the brain.

The present invention relates to a method for establishing a discriminating index of two different given ischemic status, comprising:
  determining ischemic status of a first brain region having a first given ischemic status according to the method for determining ischemic status of a brain region for obtaining the relative decrease of the diffusion magnitude of the first brain region ($L_{i1}$) to the diffusion magnitude of the normal brain tissue ($L_{n1}$);
  determining ischemic status of a second brain region having a second given ischemic status according to the method for determining ischemic status of a brain region for obtaining the relative decrease of the diffusion magnitude of the second brain region ($L_{i2}$) to the diffusion magnitude of the normal brain tissue ($L_{n2}$); and
  analyzing the relative decrease of $L_{i1}$ to $L_{n1}$ and the relative decrease of $L_{i2}$ to $L_{n2}$ in statics to obtain a threshold value of the relative decrease of diffusion magnitude for discriminating against each other as the discriminating index of two different given ischemic status.

Preferably, the first given ischemic status or the second given ischemic status is defined according to cerebral blood flow as mentioned above.

In one preferred embodiment of the invention, the first given ischemic status is ischemic penumbra, and the second given ischemic status is infarct core. In one another preferred embodiment of the invention, the first given ischemic status is normal and the second given ischemic status is ischemic penumbra.

Preferably, the first brain region and the second brain region belong to the same brain tissue type.

The present invention relates to a discriminating index of two different given ischemic status, which is established by the method for establishing a discriminating index of two different given ischemic status.

The present invention relates to a method for identifying ischemic status of a test brain region, comprising:
  determining ischemic status of the test brain region according to the method for determining ischemic status of a brain region for obtaining a relative decrease of $L_{it}$ to $L_{nt}$;
  comparing the relative decrease of $L_{it}$ to $L_{nt}$ with the discriminating index of two different given ischemic status as mentioned above to identify the ischemic status of the test brain region.

The invention provides a clinical tool for assessing stroke onset time and an objective index for the golden hour of acute ischemic stroke, which is helpful for the clinical judgement of surgical intervention.

The present invention relates to a method for assessing stroke onset time of a brain region, comprising:
  acquiring magnetic resonance diffusion tensor matrices of the brain region and of a normal brain tissue, wherein the normal brain tissue and the brain region belong to the same brain tissue type;
  obtaining pure anisotropy (q) of the brain region ($q_i$) and pure anisotropy of the normal brain tissue ($q_n$) from the magnetic resonance diffusion tensor matrices; and
  calculating a relative decrease of $q_i$ to $q_n$, and the assessing stroke onset time is determined by the relative decrease of $q_i$ to $q_n$;
  wherein ischemic status of stroke is infarct core.

The present invention relates to a method for establishing an index of assessing stroke onset time, comprising:
  providing a plurality of brain regions having a plurality of given stroke onset time; wherein the plurality of brain regions belong to the same brain tissue type;
  assessing stroke onset time of the plurality of brain regions having the plurality of given stroke onset time according to the method for assessing stroke onset time of a brain region for obtaining the plurality of relative decrease of $q_i$ to $q_n$;
  obtaining a curve of the relative decrease of $q_i$ to $q_n$ versus stroke onset time as the index of assessing stroke onset time.

Preferably, the relative decrease of $q_i$ to $q_n$ is $(q_i-q_n)/q_n \times 100\%$.

Preferably, for each brain tissue type, a specific index of assessing stroke onset time is established. For example, an index in the superficial cortex, white matter, or subcortical tissue is established separately.

The present invention relates to an index of assessing stroke onset time, which is established by the method for establishing an index of assessing stroke onset time.

The present invention relates to an index group comprising a plurality of the indices of assessing stroke onset time as mentioned above.

The present invention relates to a method for assessing stroke unset time of a test brain region, comprising:
- assessing stroke unset time of the test brain region according to the method for assessing stroke onset time of a brain region for obtaining the relative decrease of $q_{it}$ to $q_{nt}$;
- analyzing the relative decrease of $q_{it}$ to $q_{nt}$ with the index of assessing stroke onset time or index group as mentioned above to assessing the stroke unset time of the test brain region.

The following examples are provided to aid those skilled in the art in practicing the present invention.

EXAMPLES

Materials and Methods
Animal Preparations

The experiment procedure was approved by the local Institute of Animal Care and Utilization Committee. Eleven male Sprague-Dawley rats (250-300 g; National Laboratory Animal Center, Taiwan) were prepared by permanent occlusions of unilateral MCA using the intra-luminal suture as proposed by Chiang et al. (Chiang T, Messing R O, Chou W-H. Mouse model of middle cerebral artery occlusion. Journal of visualized experiments: JoVE 2011). Three of eleven rats died within 6.5 hours after MCAo and were therefore excluded from the subsequent analysis. One of the eight included rats died after the 24-hour imaging.

Magnetic Resonance Imaging

All MRI animal experiments were performed in a 7T scanner (PharmaScan 70/16; Bruker, Germany). The rats were maintained under anesthesia using 1.5-2% isoflurane with an oxygen flow of 1 L/min. Rectal temperature were kept at 37° C. by infusing warm air through the magnet bore. T2-weighted imaging (T2WI), diffusion-weighted imaging (DWI), DTI, and dynamic susceptibility contrast (DSC) perfusion imaging were performed at eight time points, starting from 0.5 hour after MCAo, then repeated every hour until 6.5 hours, with a final 24-hour imaging performed for the assessment of the final infarct volume, in accordance with methods published by Brûatane et al. (Brûatane B T, Walvick R P, Corot C, Lancelot E, Fisher M. Characterization of gadolinium-based dynamic susceptibility contrast perfusion measurements in permanent and transient mcao models with volumetric based validation by casl. J. Cereb. Blood Flow Metab. 2010; 30:336-342). One hundred percent normobaric hyperoxia (NBO) by a face mask was applied post MCAo and continued for 6.5 hours to prolong the perfusion/diffusion mismatch evolution (Henninger N, Bouley J, Nelligan J M, Sicard K M, Fisher M. Normobaric hyperoxia delays perfusion/diffusion mismatch evolution, reduces infarct volume, and differentially affects neuronal cell death pathways after suture middle cerebral artery occlusion in rats. J. Cereb. Blood Flow Metab. 2007; 27:1632-1642). T2WI was acquired using TR/TE of 6000/80 ms and slice thickness of 1 mm with in-plane resolution of 0.2×0.2 mm2. Multi-shot echo-planar imaging technique was used for DWI with b factors of 0 and 1100 s/mm2. DSC imaging was estimated by a bolus injection of Gd-DTPA (0.3 mmol/kg, Magnevist, Bayer Schering Pharma, Germany) with a serial gradient-echo echo-planar imaging using TR/TE of 1000/10 ms, flip angle of 90 degrees, and 40 repetitions. DTI were acquired using multi-shot echo-planar imaging, including 6 volumes with diffusion gradients applied along 6 non-collinear orientations (b=1100 s/mm$^2$) and one volume without diffusion weighting. The scanning parameters were TR/TE of 10,000/23 ms, $\Delta/\delta$ of 12/4 ms, and 6 averages. All data were zero-filled to generate images with a resolution of 128×128 pixels.

Data Analysis
Calculation of Apparent Diffusion Coefficient (ADC), rCBF, and FA Maps The ADC, rCBF, and FA maps at each time point were calculated using in-house MATLAB (MathWorks, Natick, MA) scripts. The ADC map was calculated using DWIs based on Stejskal-Tanner equation. For rCBF, the concentration-time curves were obtained from the signal-time curves of DSC MrI followed by a gamma-variate fitting for the recirculation removal. FA maps were calculated from the DTI as follows:

$$FA = \sqrt{\frac{3}{2}} \frac{\sqrt{(\lambda_1 - \lambda)^2 + (\lambda_2 - \lambda)^2 + (\lambda_3 - \lambda)^2}}{\sqrt{\lambda_1^2 + \lambda_2^2 + \lambda_3^2}} = \sqrt{\frac{3}{2}} \frac{q}{L}$$

where $\lambda_i$ were the eigenvalues of the diffusion tensor matrix and $\lambda$ was the mean diffusion. The scalar measures q and L represented pure diffusivity and magnitude diffusion, respectively (Wang W, Steward C, Desmond P. Diffusion tensor imaging in glioblastoma multiforme and brain metastases: The role of p, q, 1, and fractional anisotropy. Am. J. Neuroradiol. 2009; 30:203-208).

Delineation of IP and IC

Figure 6A:
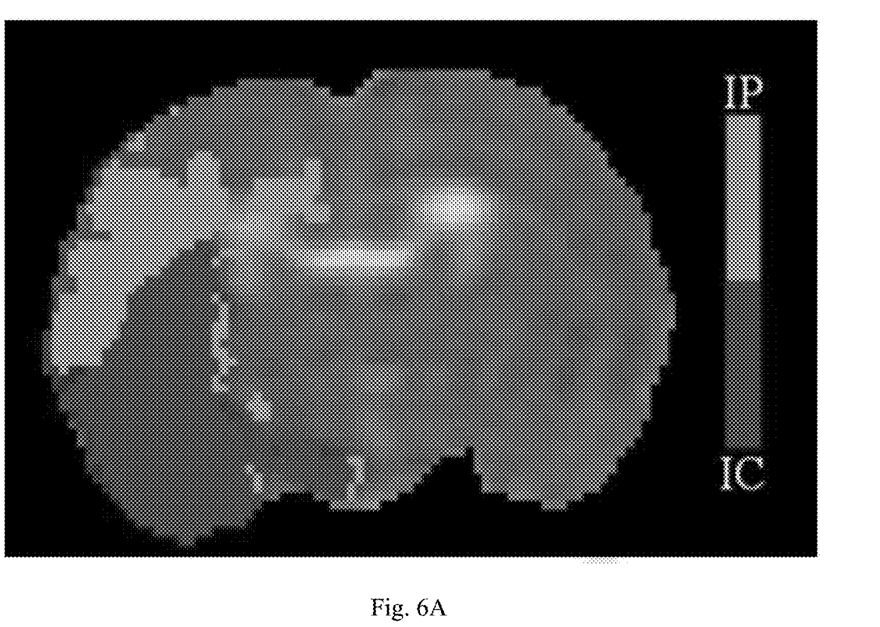
FIGS. 6A to 6C show representative perfusion/diffusion mismatch (FIG. 6A) by coregistration of an rCBF map (FIG. 6B) and an ADC map (FIG. 6C). The perfusion deficit was determined using a reduction of 46% of the rCBF compared to the contralateral hemisphere. Abnormal ADC was defined using a reduction of 30% of the contralateral hemisphere with the exclusion of the ventricles.
Figure 6B:
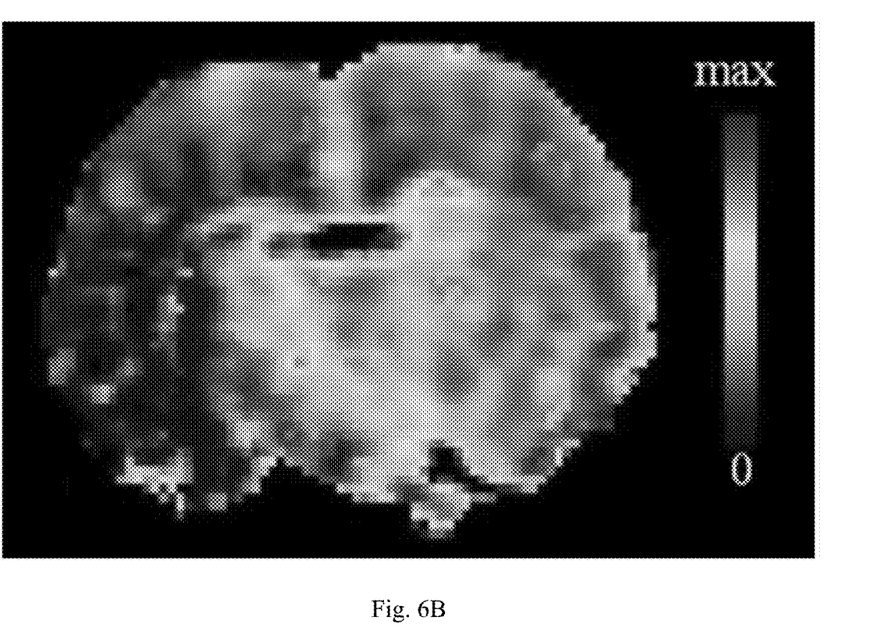
Figure 6C:
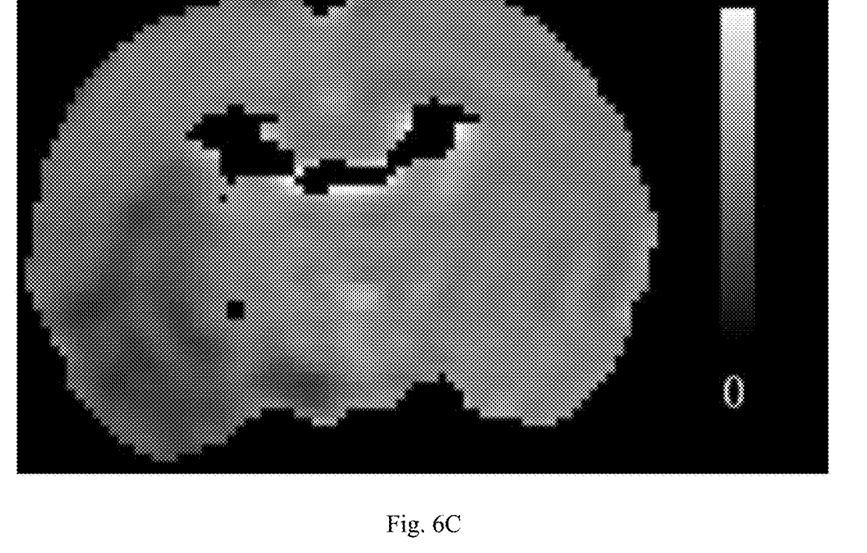

Perfusion deficit was first defined, based on the criteria that the CBF-defined lesion volume at 3 hours was equal to the infarct volume at 24 hours (Meng X, Fisher M, Shen Q, Sotak C H, Duong T Q. Characterizing the diffusion/perfusion mismatch in experimental focal cerebral ischemia. Ann. Neurol. 2004; 55:207-212). Because NBO can cause a reduction of CBF in normal brain and improvement of CBF in ischemic regions (Henninger N, Bouley J, Nelligan J M, Sicard K M, Fisher M. Normobaric hyperoxia delays perfusion/diffusion mismatch evolution, reduces infarct volume, and differentially affects neuronal cell death pathways after suture middle cerebral artery occlusion in rats. J. Cereb. Blood Flow Metab. 2007; 27:1632-1642), a lower CBF threshold of 46% reduction was used in this study to identify the CBF deficits (Shen Q, Meng X, Fisher M, Sotak C H, Duong T Q. Pixel-by-pixel spatiotemporal progression of focal ischemia derived using quantitative perfusion and diffusion imaging. J. Cereb. Blood Flow Metab. 2003; 23:1479-1488). Abnormal ADC was defined using a reduction of 30% of the contralateral hemisphere with the exclusion of the ventricles (Henninger N, Bouley J, Nelligan J M, Sicard K M, Fisher M. Normobaric hyperoxia delays perfusion/diffusion mismatch evolution, reduces infarct volume, and differentially affects neuronal cell death pathways after suture middle cerebral artery occlusion in rats. J. Cereb. Blood Flow Metab. 2007; 27:1632-1642, and Shen Q, Meng X, Fisher M, Sotak C H, Duong T Q. Pixel-by-pixel spatiotemporal progression of focal ischemia derived using quantitative perfusion and diffusion imaging. J. Cereb. Blood Flow Metab. 2003; 23:1479-1488). To delineate the areas of IC and IP, the rCBF map was first co-registered to the ADC map. IP was then defined as regions showing rCBF values <54% and ADC>70%, and IC was identified as regions showing rCBF values <54% and ADC<70% of the contralateral homologous brain (FIG. 6). The rCBF and ADC of normal tissue (NT) were defined as the averages of the homologous areas of IP and IC values in the contralateral normal hemisphere.

Topographic Classification of Brain Tissue Types

Figure 7:
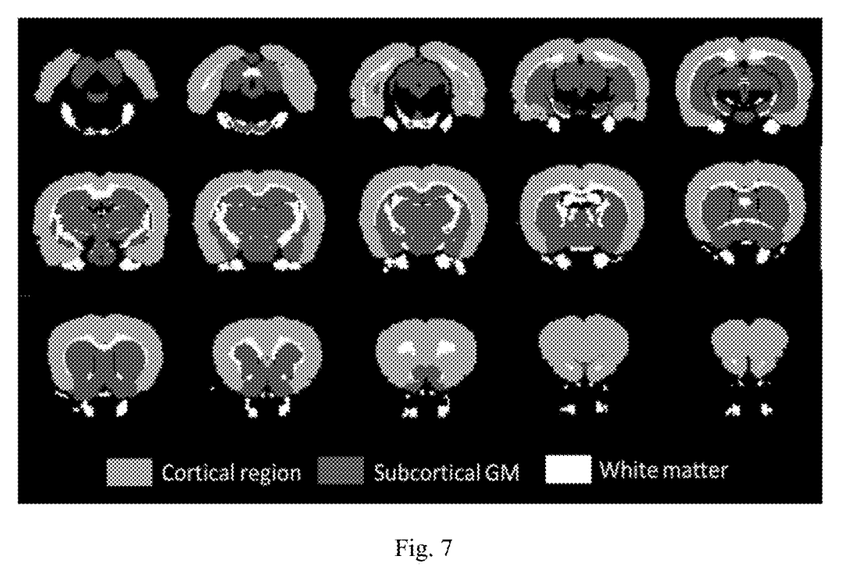
FIG. 7 shows spatial maps of identified cortical (light grey), subcortical GM (dark gray), and white matter (white).

Previous studies have shown variable tissue responses to the ischemic injury among cortical, subcortical gray matter (GM) and white matter (WM) (Bhagat Y A, Emery D J, Shuaib A, Sher F, Rizvi N H, Akhtar N et al. The relationship between diffusion anisotropy and time of onset after stroke. J. Cereb. Blood Flow Metab. 2006; 26:1442-1450, and Carano R A, Li F, Irie K, Helmer K G, Silva M D, Fisher M et al. Multispectral analysis of the temporal evolution of cerebral ischemia in the rat brain. J. Magn. Reson. Imaging 2000; 12:842-858). In this study, we applied an atlas-based tissue classification method during image processing to identify the tissue types within each image voxel for each rat model. Specifically, a FA template of Sprague-Dawley rat brain (Papp E A, Leergaard T B, Calabrese E, Johnson G A, Bjaalie J G. Waxholm space atlas of the sprague dawley rat brain. Neuroimage 2014; 97:374-386) was co-registered and resampled to the FA map of the rats using a 12-parameter affine transformation implemented by the FLIRT toolbox (Jenkinson M, Bannister P, Brady M, Smith S. Improved optimization for the robust and accurate linear registration and motion correction of brain images. Neuroimage 2002; 17:825-841). The tissue atlas originally proposed by Papp et al. differentiates rat brain into 32 WM regions and 40 GM regions (Papp E A, Leergaard T B, Calabrese E, Johnson G A, Bjaalie J G. Waxholm space atlas of the sprague dawley rat brain. Neuroimage 2014; 97:374-386). We further categorized 37 cerebral GM regions into cortical and subcortical GM regions using the corpus callosum and external capsule as the border landmarks (FIG. 7). Finally, the relative DTI matrices, as compared to the contralateral homologous tissue, were calculated as follows: $rX = (X_{ipsilateral} - X_{contralateral})/X_{contralateral}$, where X indicates the value of indices (FA, L or q value).

Statistical Analysis

Statistical analyses were performed to determine whether the post-MCAo DTI matrices can be used to discriminate IP from IC, and NT regardless of the time effect. One-way analysis of variance (ANOVA) model with post hoc analysis was applied to examine whether the means of DTI matrices within the IP, IC, and NT regions were significantly different at each imaging time point. Receiver operating characteristic (ROC) curve analysis was performed to determine the optimal threshold of rL to differentiate regions among IC, IP, and NT at 1.5 hours. The sensitivity, specificity, and accuracy were then calculated for the selected optimal thresholds. Nonlinear regression analysis using an exponential function to minimize the least squares was employed to reveal the relationship between the rq values and the time after stroke (Marquardt D W. An algorithm for least-squares estimation of nonlinear Parameters. Journal of the society for Industrial and Applied Mathematics 1963; 11:431-441).

Results

Evolutions of DTI Matrices Among Tissue Types

Figure 1A:
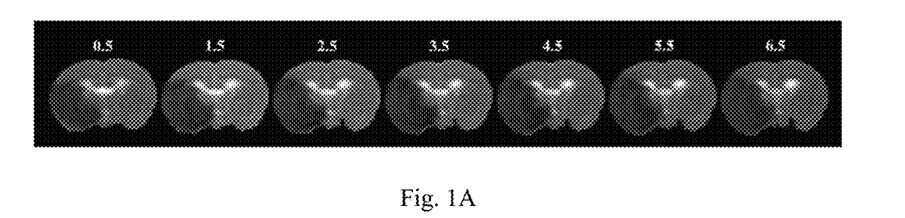
Figure 1B:
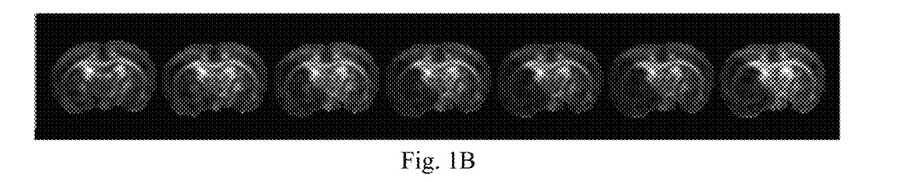
Figure 1C:
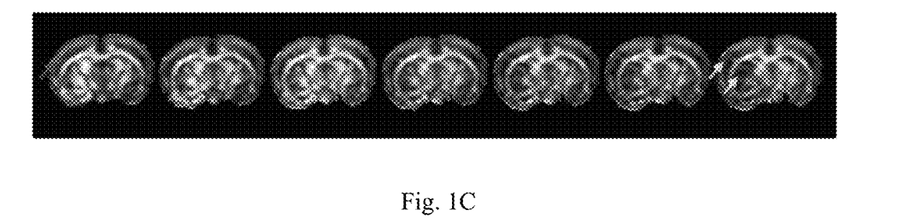
Figure 1D:
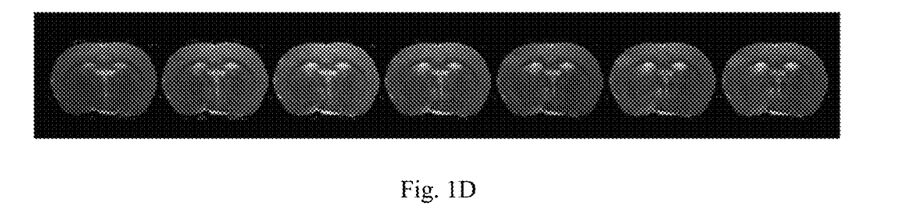
Figure 2A:
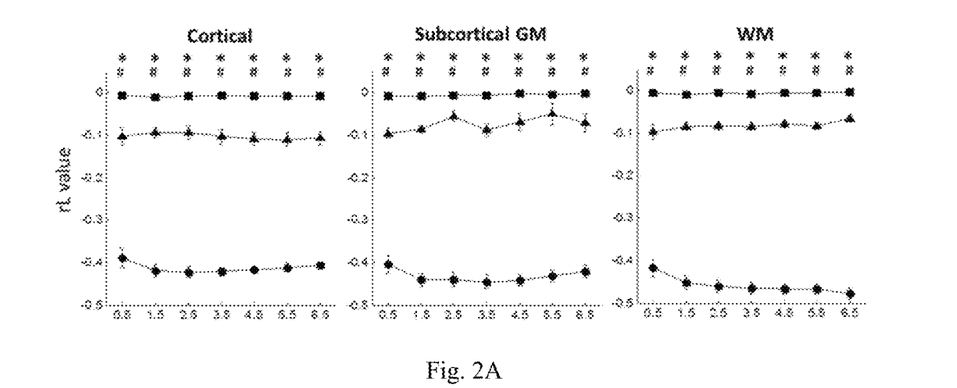
FIGS. 2A to 2C show temporal evolutions of rL (FIG. 2A), rq (FIG. 2B), and rFA (FIG. 2C) in cortical (left column), subcortical GM (middlecolumn), and WM regions (right column), respectively. In these figures, * indicates the significant difference between IP and NT ($p<0.05$), and #represents significant difference between IP and IC ($p<0.05$). Error bars are SEM.
Figure 2B:
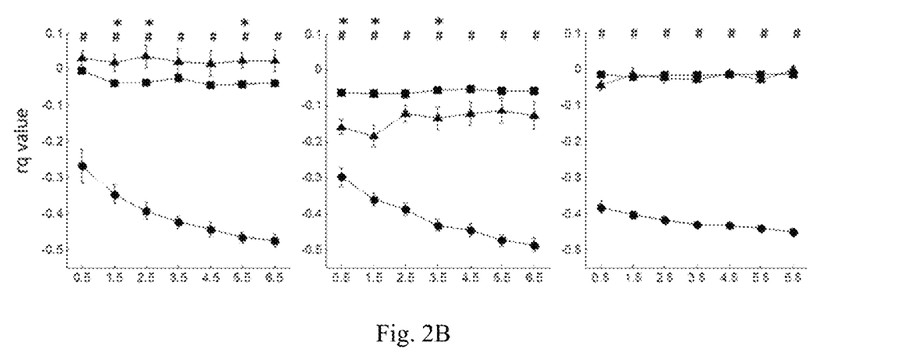
Figure 2C:
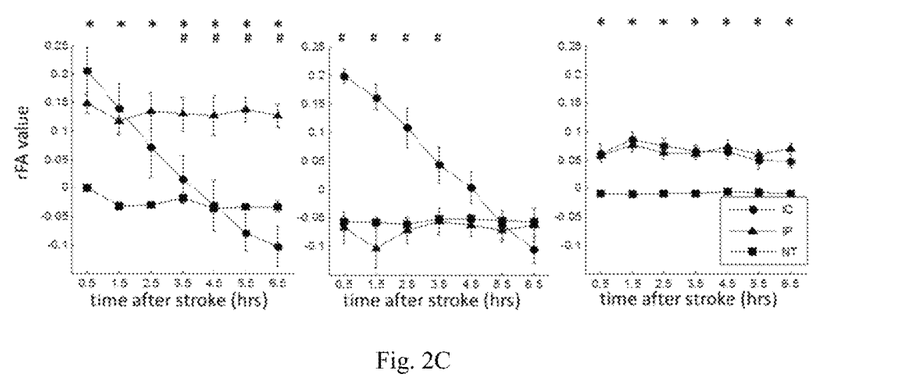
Figure 3A:
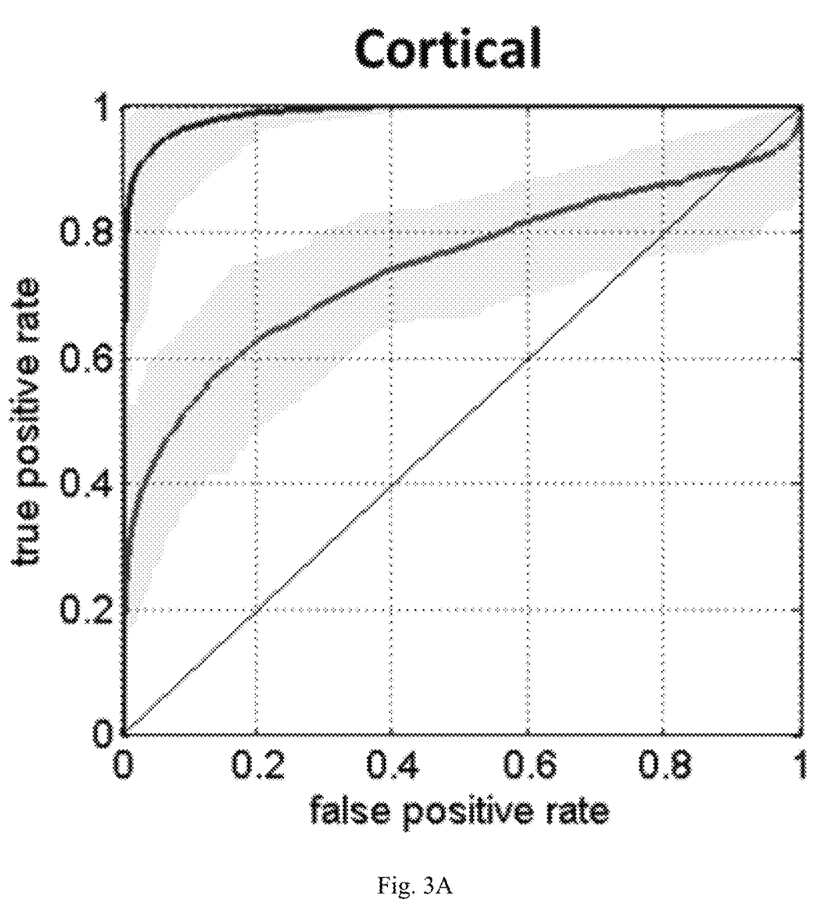
FIGS. 3A to 3C show ROC curves in discriminating IP from IC (blue curves) and NT (red curves) for cortical (FIG. 3A), subcortical GM (FIG. 3B), and WM (FIG. 3C) using rL values. In these figures, gray areas indicate the range for eight rats.
Figure 3B:
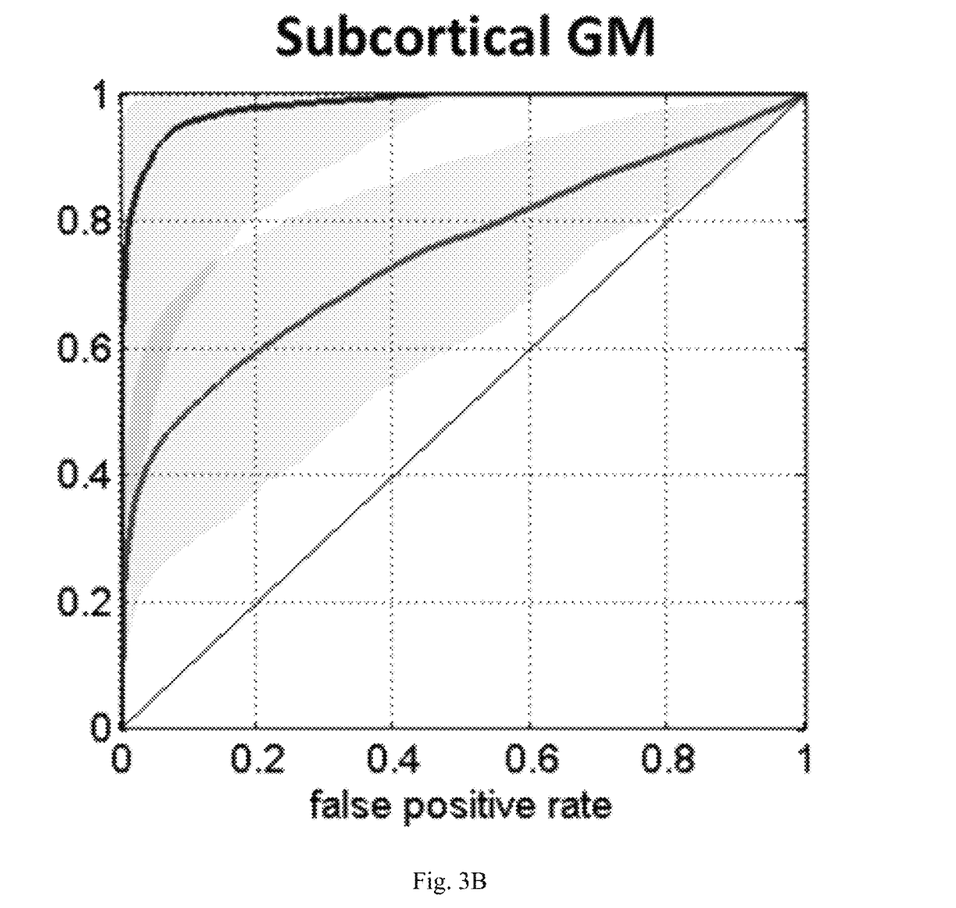
Figure 3C:
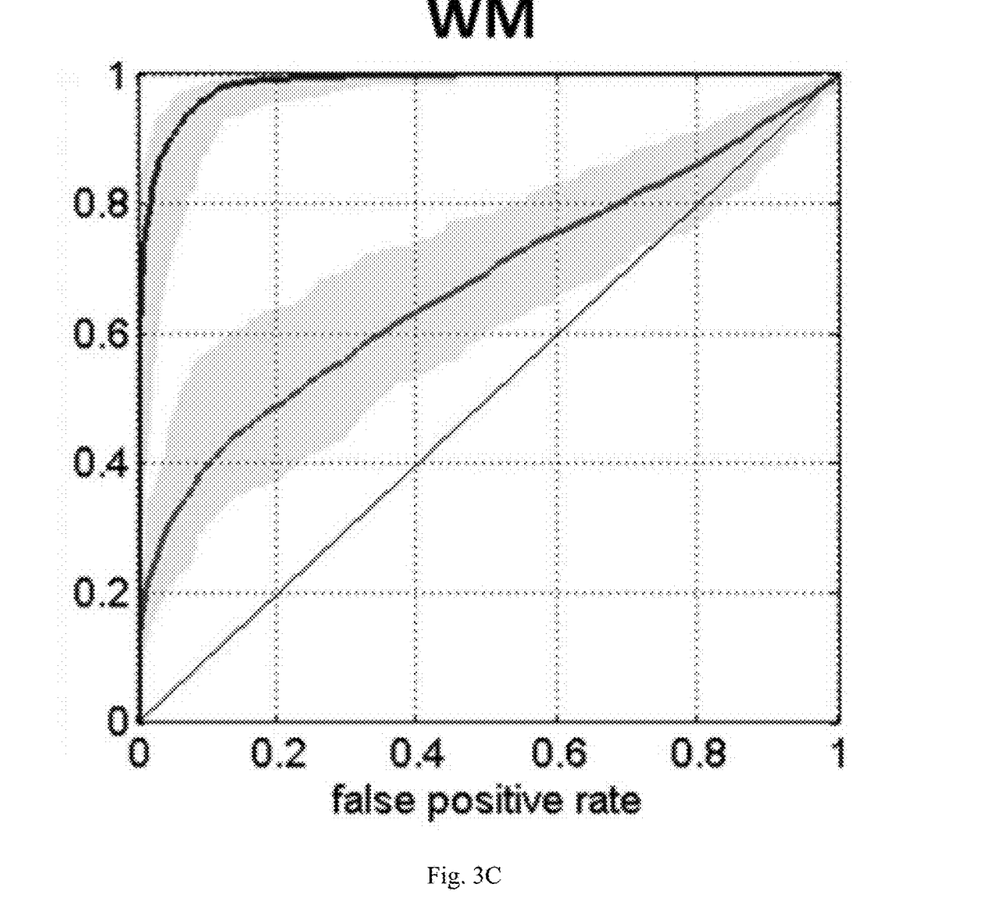

FIG. 1D illustrates the progressive slight increase of ischemic regions over time on T2WI after MCAo. The L and q maps demonstrated consistent hypointensity changes in the ischemic areas over all time points (FIGS. 1A and 1B). Meanwhile, FA maps exhibited an initial elevation of FA value at 0.5 hour in the ischemic region and a later reduction at 6.5 hours after MCAo (FIG. 1C). The FA evolution depends on the changes of rL and rq values. For instance, the evolutions of rL value in IC were stagnant (with an average reduction of 41.28% and 43.25% in cortical and subcortical GM, respectively) (FIG. 2A). However, the rq value in IC exhibited a monotonic decrease from a reduction of 28% at 0.5 hour to 50% at 6.5 hours in both cortical and subcortical GM (FIG. 2B). Accordingly, the relatively small reduction of rq as compared to a larger reduction of rL resulted in a 20% increase of FA in the cortical and subcortical GM IC regions during the first 3.5 hours (FIG. 2C). At 6.5 hours, the reduction of rq value became greater than the reduction of rL, leading to a marked decrease in FA (negative rFA values) in the same region. On the other hand, the evolution of rFA in WM IC was relatively stable with a 6.41±1.34% increment due to the similar decay profiles of rL and rq (right column in FIG. 2).

Discrimination of IP from IC and IP from NT by rL

Significant differences (p<0.05) in rL values were found between IP and IC, and between IP and NT for all tissue subtypes (FIG. 2A). The ROC curves and the optimal rL thresholds for discriminating IP from IC and from NT were shown in FIG. 3, and Table 1, respectively. The threshold for discriminating IP from IC is relatively constant (about −29%). Whereas, the optimal rL threshold for separating IP from NT shows a significant difference between cortical and subcortical regions (p=0.022). The results indicate that the tissue-specific rL threshold is an important factor in the discrimination between IP and NT. The overall performance of tissue-specific rL thresholds is listed in Table 2, which shows excellent discrimination of IP from IC by rL in all tissue subtypes (average accuracy >0.95). The discrimination performance between IP and NT is good in the subcortical GM and cortical region, with an average accuracy of 0.83 and 0.79, respectively, and moderate in the WM region with accuracy at 0.68.

TABLE 1

Optimal rL threshold (%) in discriminating IC, IP, and NT for each rat

| Rats | #1 | #2 | #3 | #4 | #5 | #6 | #7 | #8 | Average (std) |
|---|---|---|---|---|---|---|---|---|---|
| IP vs. IC | | | | | | | | | |
| Cortical | −30.01 | −32.31 | −29.45 | −26.76 | −28.70 | −33.58 | −27.93 | −26.80 | −29.44 (2.31) |
| Subcortical | −24.84 | −29.07 | −28.81 | −29.02 | −25.92 | −28.45 | −30.08 | −28.07 | −28.03 (1.65) |
| WM | −31.19 | −28.28 | −25.72 | −27.39 | −27.02 | −27.25 | −29.04 | −32.34 | −28.53 (2.09) |
| IP vs. NT | | | | | | | | | |
| Cortical | −6.62 | −8.74 | −10.63 | −13.41 | −10.46 | −9.43 | −11.63 | −10.74 | −10.21 (1.89) |
| Subcortical | −8.36 | −10.61 | −14.04 | −12.04 | −13.15 | −15.92 | −12.60 | −13.38 | −12.51 (2.13) |
| WM | −10.92 | −12.61 | −8.50 | −17.60 | −10.47 | −11.62 | −12.22 | −11.53 | −11.93 (2.45) |

In Table. 1, IC=infarct core, IP=ischemic penumbra, NT=normal tissue, WM=white matter, std=standard deviation.

TABLE 2

Discrimination performance based on rL values

| | Accuracy | | | Sensitivity | | | Specificity | | |
|---|---|---|---|---|---|---|---|---|---|
| | Mean | Max. | Min. | Mean | Max. | Min. | Mean | Max. | Min. |
| IP vs. IC | | | | | | | | | |
| Cortical | 0.95 | 0.98 | 0.81 | 0.94 | 0.99 | 0.79 | 0.93 | 0.99 | 0.83 |
| Subcortical | 0.97 | 0.99 | 0.91 | 0.98 | 0.99 | 0.94 | 0.92 | 0.99 | 0.75 |
| WM | 0.95 | 0.97 | 0.91 | 0.94 | 0.98 | 0.81 | 0.93 | 0.99 | 0.88 |
| IP vs. NT | | | | | | | | | |
| Cortical | 0.79 | 0.87 | 0.70 | 0.42 | 0.63 | 0.22 | 0.95 | 0.98 | 0.86 |
| Subcortical | 0.83 | 0.89 | 0.74 | 0.40 | 0.52 | 0.14 | 0.97 | 0.99 | 0.94 |
| WM | 0.68 | 0.77 | 0.60 | 0.40 | 0.56 | 0.26 | 0.91 | 0.99 | 0.83 |

In Table. 2, IC=infarct core, IP=ischemic penumbra, NT=normal tissue, WM=white matter, Max=maximum, Min=minimum, Sensitivity is calculated as the proportion of positives that the perfusion/diffusion-defined IP voxels are correctly identified as IP by using the rL values; Specificity is calculated as the proportion of negatives that the perfusion/diffusion-defined IC or NT voxels are correctly identified as IC or NT based on the rL values; Accuracy is defined as the proportion of true positives and true negatives to the overall testing voxels.

The representative maps of the rL-defined IC and IP (FIG. 4B) as compared with the corresponding perfusion/diffusion-defined IC and IP (FIG. 4A) of a rat suggested that the rL-defined maps can successfully segment the ischemic regions into IP and IC. The T2WIs at 24 hours showed complete infarct of the ipsilateral MCA territory.

Exponential Decay of q-Value in Cortical IC

A reduction of the rq value in cortical IC from −26.9% to −47.6% within the 6.5 hours after stroke onset was observed (FIG. 2B). A nonlinear regression analysis was further applied to estimate the relationship between the rq values and the time after stroke. The passed time after stroke onset can be assessed by the equation, passed time (in minutes)=1.636×exp (−0.115×rq). This exponential decay of rq value over time suggests that rq value in cortical IC can be a potential surrogate marker to determine the stroke onset time at hyeracute stage, for instance, an rq value reduction smaller than 44.6% predict an acute stroke onset less than 4.5 hours (red dashed lines in FIG. 5).

According to the invention, three main findings are important to clinical stroke management, including: 1) The brain tissue subtypes (cortical, subcortical GM, and WM) exhibited different responses to ischemic injury which can be characterized by the temporal evolutions of q and L; 2) Discrimination of IP from IC and NT by rL values showed comparable results to the conventional perfusion/diffusion mismatch; 3) A reduction of 44.6% of rq value can be used as a biomarker to determine the hyperacute stroke onset less than 4.5 hours.

The existence of collateral circulation may interpret the lesser decrease of diffusion anisotropy in cortical IC (−26.89% of rq) as compared to the larger reduction of anisotropy in WM IC (−38.20% of rq) at 0.5 hours after MCAo (FIG. 2B).

Figure 4A:
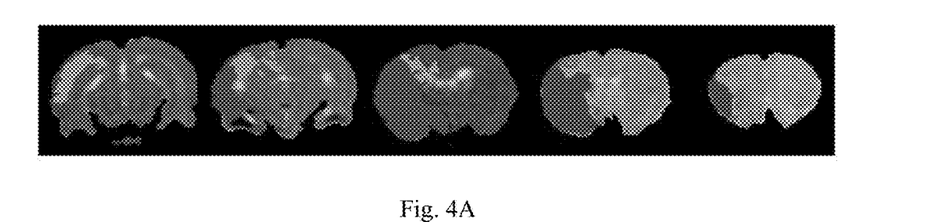
FIGS. 4A and 4C show IC (red) and IP (green) regions defined by perfusion-diffusion mismatch (FIG. 4A) and proposed L defined method (FIG. 4B) a rat at 90 min after MCAO. The 24 hr-T2WIs are also displayed to show the final infarct regions (FIG. 4C). A severe edema extending to normal hemisphere is observed in 24 hr-T2WIs.
Figure 4B:
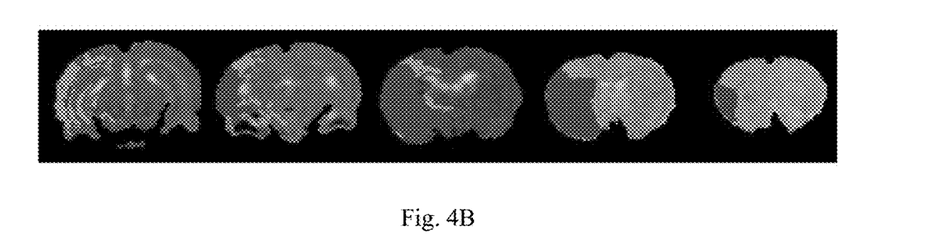
Figure 4C:
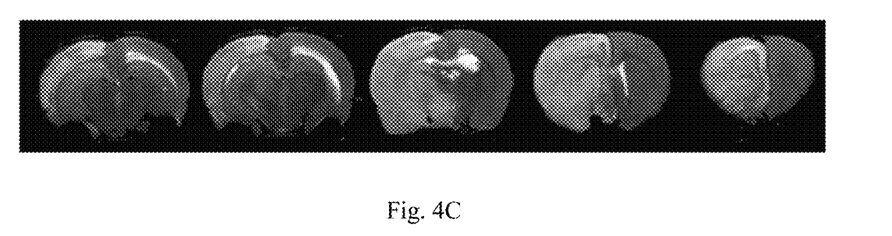

L-defined maps, calculated from a single DTI sequence, is helpful for discriminating IP from IC (with accuracy >0.95) which is comparable to the perfusion/diffusion mismatch during hyperacute stroke (FIG. 2A and FIG. 4). For the discrimination between IP and NT, the tissue-specific rL thresholds can ensure sufficient accuracies (larger than 0.79) for tissues in the subcortical GM and cortical region, however, only moderate accuracy can be achieved in the WM areas (0.68, see Table 2). This can be explained by the fact that the WM is a relatively scanty area in rat brain with limited image pixels, leading to increased vulnerability to inaccuracy.

It also showed a 20% increase of rFA in the cortical and subcortical GM IC regions during the first 3.5 hours and a subsequent reduction to −10% at 6.5 hours after MCAo (FIG. 2C). Furthermore, in term of mathematics, FA value is determined by the interplay between q and L. Therefore, investigating the individual evolutions of q and L rather than their ratio may avoid the misinterpretations of diffusion anisotropy. It confirmed that the acute increase of FA in the cortical and subcortical GM IC regions was due to the relatively small reduction of rq as compared to a larger reduction of rL. Accordingly, the value of rq may provide a more accurate measure of changes in diffusion anisotropy caused by ischemic brain injury.

Figure 5:
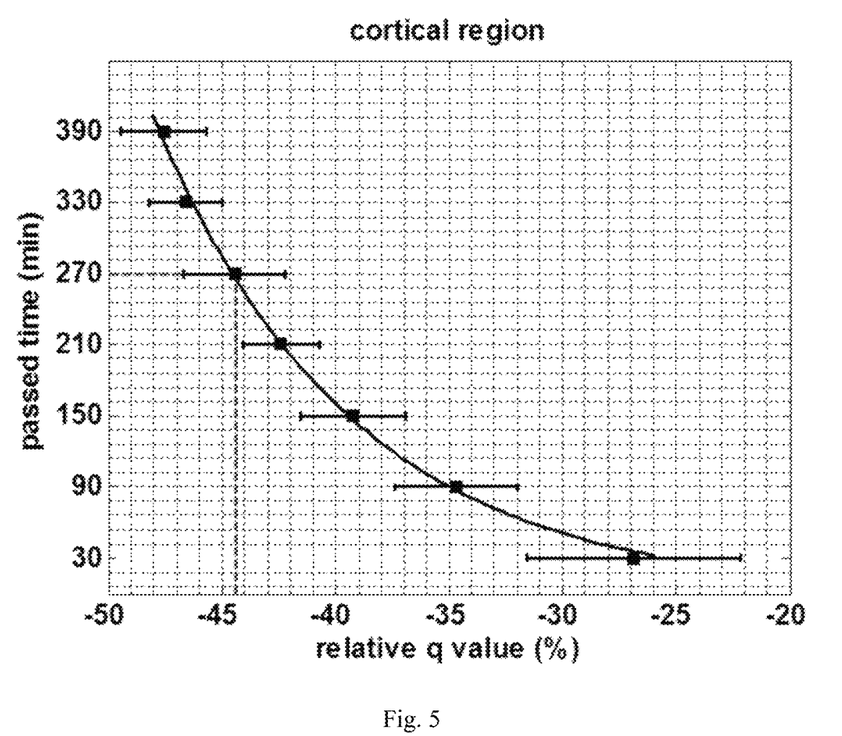
FIG. 5 shows a relationship between the rq value and the time after stroke for the cortical IC. The solid curve represents the empirical relationship, i.e., passed time=1.636*exp(−0.115*rq value), estimated by nonlinear regression analysis. The red dashed lines indicate that the 4.5-hr stroke onset can be identified by a 44.6% reduction of rq value. Error bars are SEM.

According to the invention, the evolutions of rq value in the cortical, subcortical GM, and WM IC regions all exhibited monotonic decreases within the first 6.5 hours of stroke onset (FIG. 2B). By the regression analysis, the stroke age of 4.5 hours can be estimated by an rq value of −44.6% (a 44.6% reduction) in cortical IC regions (FIG. 5). These findings suggest that rq value could be useful in evaluating stroke onset time, particular in patients with wakeup stroke.

DTI provides a quick and reliable measure to distinguish IP from IC based on rL values, and predict stroke age using the rq in cortical IC during the hyperacute phase. To our knowledge, this is the first study to demonstrate the potential utility of a single DTI sequence to substitute the conventional approach of perfusion/diffusion mismatch and help the evaluation of stroke age with unknown onset time.

While the present invention has been described in conjunction with the specific embodiments set forth above, many alternatives thereto and modifications and variations thereof will be apparent to those of ordinary skill in the art. All such alternatives, modifications and variations are regarded as falling within the scope of the present invention.

What is claimed is:

1. A method for assessing stroke onset time of a brain region, comprising:

acquiring magnetic resonance diffusion tensor matrices of the brain region and of a normal brain tissue, wherein the normal brain tissue and the brain region belong to the same brain tissue type;

obtaining pure anisotropy (q) of the brain region ($q_i$) and pure anisotropy of the normal brain tissue ($q_n$) from the magnetic resonance diffusion tensor matrices; and calculating a relative decrease of $q_i$ to $q_n$, and the assessing stroke onset time is determined by the relative decrease of $q_i$ to $q_n$;

wherein ischemic status of stroke is infarct core.

2. The method according to claim 1, which further comprises acquiring a brain tissue type map, wherein the brain tissue type map is obtained by fractional anisotropy mapping calculated from the magnetic resonance diffusion tensor matrices.

3. The method according to claim 1, wherein the brain region and the normal brain tissue belong to the same brain tissue type in an atlas-based tissue classification method.

4. The method according to claim 1, wherein the normal brain tissue is a contralateral homologous tissue of the brain region.

5. A method for establishing an index of assessing stroke onset time, comprising:

providing a plurality of brain regions having a plurality of given stroke onset time; wherein the plurality of brain regions belong to the same brain tissue type;

assessing stroke onset time of the plurality of brain regions having the plurality of given stroke onset time according to the method as claimed in claim 1 for obtaining the plurality of relative decrease of $q_i$ to $q_n$;

obtaining a curve of the relative decrease of $q_i$ to $q_n$ versus stroke onset time as the index of assessing stroke onset time.

6. An index of assessing stroke onset time, which is established by the method according to claim 5.

7. A method for assessing stroke unset time of a test brain region, comprising:

acquiring magnetic resonance diffusion tensor matrices of the test brain region and of a normal brain tissue, wherein the normal brain tissue and the test brain region belong to the same brain tissue type;

obtaining pure anisotropy (q) of the brain region ($q_{it}$) and pure anisotropy of the normal brain tissue ($q_{nt}$) from the magnetic resonance diffusion tensor matrices;

calculating a relative decrease of $q_{it}$ to $q_{nt}$;

analyzing the relative decrease of $q_{it}$ to $q_{nt}$ with the index of assessing stroke onset time according to claim 6 to assessing the stroke unset time of the test brain region.

8. The method according to claim 7, which comprises nonlinear repression analyzing the relative decrease of $q_{it}$ to $q_{nt}$ with the index of assessing stroke onset time.

* * * * *